United States Patent [19]

Giglio

[11] Patent Number: 5,417,568
[45] Date of Patent: May 23, 1995

[54] GINGIVAL CONTOURED ABUTMENT

[76] Inventor: Graziano D. Giglio, 18 E. 50th St., New York, N.Y. 10022

[21] Appl. No.: 201,530

[22] Filed: Feb. 25, 1994

[51] Int. Cl.⁶ .................. A61C 8/00; A61C 13/12; A61C 13/225
[52] U.S. Cl. .................. 433/173; 433/172; 433/174
[58] Field of Search .............. 433/172, 173, 174, 175, 433/176

[56] References Cited

U.S. PATENT DOCUMENTS

| | | | |
|---|---|---|---|
| 4,468,200 | 8/1984 | Munch | 433/174 |
| 4,531,915 | 7/1985 | Tatum, Jr. | 433/173 |
| 4,531,916 | 7/1985 | Scantlebury et al. | 435/173 |
| 5,015,186 | 5/1991 | Detsch | 433/173 |
| 5,035,619 | 7/1991 | Daftary | 433/173 |
| 5,073,111 | 12/1991 | Daftary | 433/173 |
| 5,116,225 | 5/1992 | Riera | 433/173 |
| 5,135,395 | 8/1992 | Marlin | 433/174 |
| 5,145,372 | 9/1992 | Daftary et al. | 433/173 |
| 5,169,309 | 12/1992 | Staublie et al. | 433/174 |
| 5,180,303 | 1/1993 | Hornburg et al. | 433/173 |
| 5,195,890 | 3/1993 | Johansson et al. | 433/172 |
| 5,195,891 | 3/1993 | Sulc | 433/173 |
| 5,238,405 | 8/1993 | Marlin | 433/173 |
| 5,246,370 | 9/1993 | Coatoam | 433/173 |

Primary Examiner—Nicholas D. Lucchesi
Attorney, Agent, or Firm—Kane, Dalsimer, Sullivan, Kurucz, Levy, Eisele & Richard

[57] ABSTRACT

An abutment for an implant of a dental prosthesis is contoured to follow the gingival margin.

6 Claims, 2 Drawing Sheets

GINGIVAL CONTOURED ABUTMENT

BACKGROUND OF THE INVENTION

This invention relates to prosthodontic restorations, and, particularly, dental implants or prosthesis whereby a fixture, typically titanium, is surgically implanted in the edentulous area of the alveolar bone as a substitute for a missing natural tooth root.

Today, dental restorations are frequently coupled with titanium implants placed in a patient's bone structure underlying missing teeth for the purpose of replacing the lost teeth. Osseointegration, the bonding between the bone and implant, firmly anchors the implant fixture in place to provide a secure base for the prosthesis. In this regard, a titanium transmucosal abutment is connected to the implant fixture with a screw. The abutment thereby emerges from the patient's soft tissue or gum and provides the structure upon which to mount the restoration. A restoration, shaped like a tooth and having an internally mounted cylinder, is typically connected to the abutment by either cement or a screw.

The use of dental implants has become increasingly popular since their commercial introduction. Initial attention of implant restoration of the mouth was focused on the achievement of sound integration of the titanium fixtures to the surrounding bone. Success was determined by the degree of osseointegration. As the dental community relied more and more on this field of prosthodontics, a variety of implants and appliances became available. However, the concentration on providing biocompatible fixtures in the mouth, resulted in inadequate attention being paid to providing restorations that are esthetic and integrate fully and are more compatible to the patient's gums and gum line.

In natural teeth, the gingival contour interproximally (mesial and distal) is greater than the facial or lingual contour.

In conventional fixed prosthodontics, tooth preparation for full coverage, restorations follow the contour of the gingival margin. The tooth preparation interproximally is more coronal than the facial or lingual. The tooth preparation is scalloped to follow the gingival margin mesiodistally across the facial and lingual.

All implants abutments of dental prostheses available today are the same height coronally along the gingival margin for complete 360°. The gingival portion of the conventional abutments do not follow the contour of the gingiva. Since the interproximal tissue is higher coronally, the papilla are unsupported by the abutment, and, consequently, they tend to collapse towards the abutment resulting in potential health problems, improper and undesirable gingiva contour and an esthetically unattractive gum line.

SUMMARY OF THE INVENTION

A principal objective of the present invention is to provide an abutment for a dental implant that is contoured to follow the gingival margin.

Another objective is to provide a contoured abutment of the foregoing type that possesses the following attributes:

1. Prevents collapse of the papilla onto the abutment.
2. Establishes gingival health, contour and esthetics similar to conventional crown restoration.
3. Facilitates inspection of interproximal superstructure fit.
4. Facilitates tissue manipulation during crown fabrication procedures.
5. Prevents tissue impingement during provisionalization.
6. Enhances accessibility to interproximal area during impressioning procedures.
7. Development of proper emergence profiles.
8. Maintains proper papillary integrity.

Other objects and advantages will become apparent from the following detailed description which is to be taken in conjunction with the accompanying drawings.

DETAILED DESCRIPTION OF THE PREFERRED EMBODIMENTS

Figure 1:
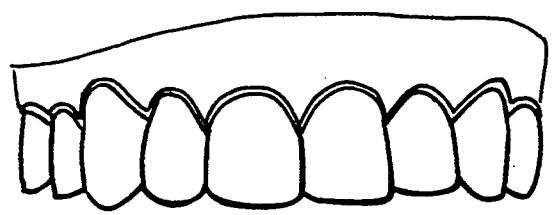
FIG. 1 is a fragmentary elevational view of natural teeth showing the gingival contour attributable to healthy gums.
Figure 2:
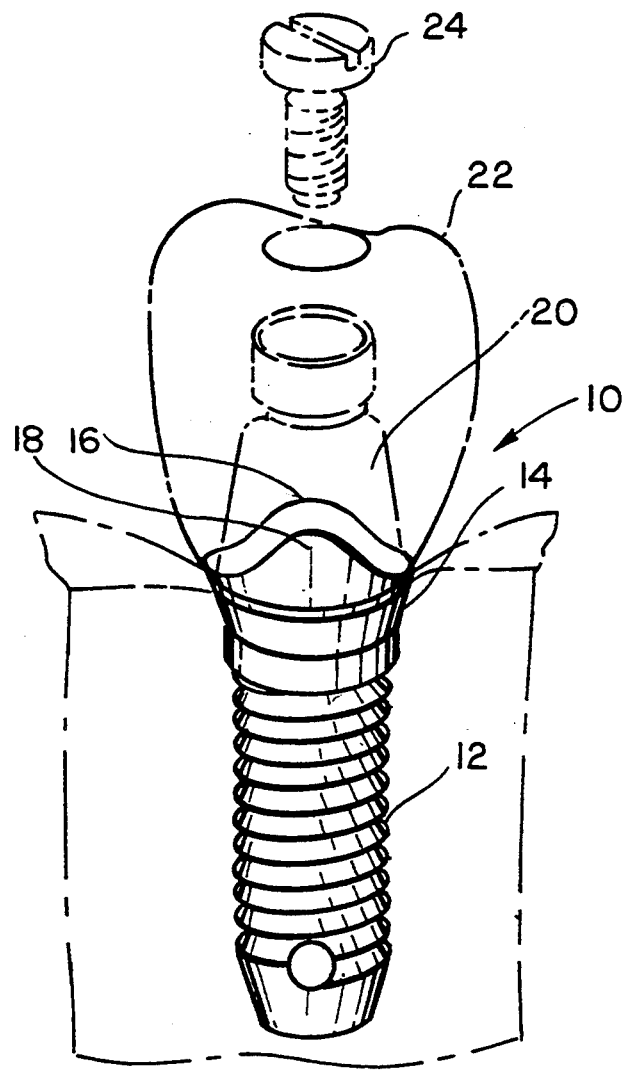
FIG. 2 is a perspective interproximal view of the dental prosthesis of this invention showing the scalloped interproximal of the abutment.

In FIG. 1, natural teeth are illustrated where the gingival contour interproximally (mesial and distal) is greater than the facial or lingual contours. Accordingly, the exemplary dental prosthesis 10 of the present invention creates gingival contours surrounding an implant prosthesis which imitate the gingival contours around natural teeth as well as around conventional fixed prosthodontic restorations. The prosthesis 10 includes an implant fixture 12 which is normally titanium and placed in a patient's bone structure. Attached to the fixture 12 in a conventional manner is abutment 14 which is scalloped or contoured such that there is a raised ridge 16 and 18 on the interproximal side of the abutment.

The abutment 14 may be fabricated from a gold alloy, titanium, or ceramic material. Attached to the abutment 14 in a conventional manner is cylinder 20 which is normally fabricated of a gold alloy. Mounted on the cylinder is a conventional porcelain restoration 22 connected thereto by screw 24.

The present invention contemplates scalloped contoured abutments of different configurations having collars of different sizes that would be needed to accommodate variable tissue heights. In this regard the present invention proposes a ½ mm abutment collar on the unscalloped portion of the abutment (facial and lingual). As previously indicated, the contemplated different abutment configurations can also be fabricated from gold alloy, titanium alloy, or ceramic material. As in existing dental prostheses, the corresponding lab analogs, abutment screws, impression copings, gold cylinders and provisionalization components are usable with the abutment of this invention.

As will be apparent to those skilled in the art, two possible Hex positions must be considered when relating the interproximal of the abutment 14 to that of the fixture 12 as shown in FIG. 4. The Hex of an implant fixture 12 is normally never placed into the bone in the same orientation in relation to the interproximal of the adjacent teeth. Two different abutments must be fabricated to accommodate the variable positioning of fixture placement.

Figure 4A:
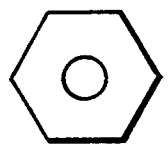
FIG. 4A and 4B are a schematic representation of two possible fixture Hex positions.
Figure 4B:
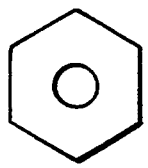

Possible fixture Hex positions as shown in FIG. 4A and 4B are as follows:

| | |
|---|---|
| Position 1: (FIG. 4A) | One side of the fixture Hex is placed parallel or nearly parallel to the facial or lingual cortical plates. |
| Position 2: (FIG. 4B) | No side of the fixture Hex is parallel to the facial or lingual cortical plates. |

Figures 5A, 5B:
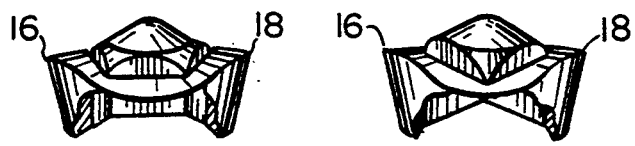
FIG. 5A and 5B are schematic representations of two corresponding positions of the abutment relating the scalloped contour with the internal Hex that mates with the external Hex of the fixture.

The differences between Position 1, and Position 2, is how the internal Hex of the abutment relates to the scalloped contoured position of the abutment of FIG. 5A and 5B.

In Position 1 of FIG. 5A, the scalloped portion of the abutment is aligned or related to the corner of the internal Hex of the abutment, as well as the Hex of the fixture. In Position 2 of FIG. 5B, the scalloped portion of the abutment relates to the side of the internal Hex of the abutment as well as the Hex of the fixture.

A mathematical calculation shows that the difference between an abutment in Position 1, or in Position 2 of FIG. 5, is as follows:

Diameter of the gingival portion of the abutment = 4.0 mm $$\text{The circumference of the abutment} = \pi * \text{diameter}$$
$$= 3.14 * 4.0 \text{ mm}$$
$$= 12.56 \text{ mm}$$

Since a circle is 360 degrees and a hexagon has an internal angle of 60 degrees, the greatest difference possible between the two abutment positions is 30 degrees.

360 degrees ÷ 30 degrees = 12

30 degrees is 1/12 of the circle.

Figure 3:
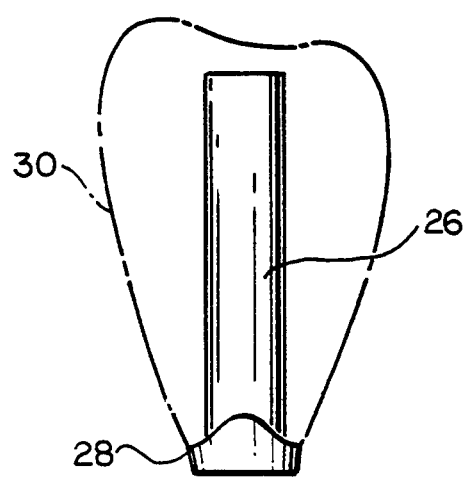
FIG. 3 is an elevational view of a sleeve for receiving a cementable restoration and which is attachable with an implant fixture that is provided with a scalloped interproximal cast contour.
Figure 6:
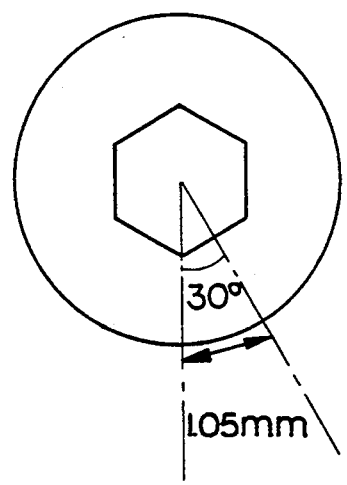
FIG. 6 is a schematic view of the abutment.

Therefore, 1/12 *12.56 mm = 1.05 mm as shown in FIG. 6. Clinically, at the abutment level the difference between the two abutments is 1.05 mm. The two abutments are necessary so that the scalloped portion of the abutment does not fall on the facial surface of the restoration thereby compromising the esthetic result. The scalloped portion of the abutment must fall on the interproximal surface of the restoration irregardless of the implant fixture orientation. For cementable and difficult angulation situations, a castable waxing sleeve (made of a resin) 26 similar to the UCLA type abutment would also be necessary as shown in FIG. 3. This would entail waxing to a sleeve with scalloped interproximal contours 28 and casting this in a gold alloy to fabricate the necessary custom abutment. Next, the laboratory technologist would fabricate a custom gold cylinder or coping over the custom abutment as in conventional crown and bridge construction. This coping could be cemented over the scalloped abutment, if so desired, rather than utilizing a screw-retained prosthesis thereby providing a cemented restoration 30.

Thus, the several aforenoted objects and advantages have been effectively attained. Although several somewhat preferred embodiments have been disclosed and described in detail herein, it should be understood that this invention is in no sense limited thereby and its scope is to be determined by that of the appended claims.

I claim:

1. A dental prosthesis comprising a fixture for insertion in an accommodating hole in the edentulous area of the alveolar bone of a patient as a substitute for a missing natural tooth root, an abutment coupled with the fixture, the abutment having a scalloped contour adapted to follow the gingival margin of the patient, the scalloped contour of the abutment facing in a direction away from said fixture and having a first scallop contour portion adapted to interproximally correspond to the mesial and distal contour of adjacent gingiva, said first contour portion being raised relative to a second scallop contour portion which is adapted to correspond to the facial and lingual contour of adjacent gingiva, and means for coupling a dental restoration to the abutment whereby the contoured abutment cooperates in preventing collapse of the papilla onto the abutment while maintaining papillary integrity.

2. The invention in accordance with claim 1 wherein the abutment has an internal Hex a flat side of which is aligned with the second contour portion of the scalloped contour.

3. The invention in accordance with claim 1 wherein the abutment has an internal Hex a corner of which is aligned with the second contour portion of the scalloped contour.

4. The invention in accordance with claim 1, wherein the coupling means includes a cylinder coupled with the abutment and which is adapted to correspond to the restoration.

5. The invention in accordance with claim 1 wherein the coupling means includes a post integral with the abutment for cementing to the restoration.

6. The invention in accordance with claim 1 wherein the first contour portion is a raised ridge.

* * * * *